US 7,039,878 B2
May 2, 2006

(12) United States Patent
Auer et al.

(10) Patent No.: US 7,039,878 B2
(45) Date of Patent: May 2, 2006

(54) APPARATUS FOR PROCESSING AND DISPLAYING PATIENT MEDICAL INFORMATION

(75) Inventors: John A. Auer, Ipswich, MA (US); Jolyn Rutledge, Amesbury, MA (US); Rand J. Monteleone, Acton, MA (US)

(73) Assignee: Draeger Medical Systems, Inc., Danvers, MA (US)

( * ) Notice: Subject to any disclaimer, the term of this patent is extended or adjusted under 35 U.S.C. 154(b) by 516 days.

(21) Appl. No.: 09/990,972

(22) Filed: Nov. 17, 2001

(65) Prior Publication Data

US 2002/0116226 A1    Aug. 22, 2002

Related U.S. Application Data

(60) Provisional application No. 60/249,574, filed on Nov. 17, 2000.

(51) Int. Cl.
*G06F 3/00* (2006.01)
(52) U.S. Cl. ........................ 715/810; 715/771
(58) Field of Classification Search ............... 345/810, 345/813, 771; 715/810, 813, 771
See application file for complete search history.

(56) References Cited

U.S. PATENT DOCUMENTS

| | | | |
|---|---|---|---|
| 4,878,175 A | 10/1989 | Norden-Paul et al. | 364/413.01 |
| 5,121,470 A | 6/1992 | Trautman | 395/140 |
| 5,262,943 A | 11/1993 | Thibado et al. | 364/413.01 |
| 5,447,164 A | 9/1995 | Shaya et al. | 128/710 |
| 5,473,536 A | 12/1995 | Wimmer | 364/400 |
| 5,682,526 A | 10/1997 | Smokoff et al. | 395/615 |
| 5,713,350 A | 2/1998 | Yokota et al. | 128/630 |
| 5,715,451 A | 2/1998 | Marlin | 395/615 |
| 5,911,132 A | 6/1999 | Sloane | 705/3 |
| 5,911,133 A | 6/1999 | Soble | 705/3 |
| 5,921,920 A | 7/1999 | Marshall et al. | 600/300 |
| 5,941,820 A | 8/1999 | Zimmerman | 600/300 |
| 5,995,937 A | 11/1999 | DeBusk et al. | 705/2 |
| 6,055,506 A | 4/2000 | Frasca, Jr. | 705/3 |
| 6,108,635 A | 8/2000 | Herren et al. | 705/2 |
| 6,167,406 A | 12/2000 | Hoskins et al. | 707/102 |
| 6,168,563 B1 | 1/2001 | Brown | 600/301 |
| 6,222,547 B1 * | 4/2001 | Schwuttke et al. | 345/419 |
| 6,263,330 B1 | 7/2001 | Bessette | 707/4 |
| 6,322,502 B1 * | 11/2001 | Schoenberg et al. | 600/300 |
| 6,581,039 B1 * | 6/2003 | Marpe et al. | 705/7 |

FOREIGN PATENT DOCUMENTS

| | | |
|---|---|---|
| WO | WO 96/27163 | 9/1996 |
| WO | WO 98/29790 | 7/1998 |

OTHER PUBLICATIONS

Solar Lab Access System General Information.

(Continued)

*Primary Examiner*—Raymond J. Bayerl
*Assistant Examiner*—Dennis Bonshock
(74) *Attorney, Agent, or Firm*—Jack Schwartz & Associates

(57) ABSTRACT

A network compatible, configurable user interface system for displaying a set of user-selectable, sequentially generated patient medical parameters, together with an associated time indication comprises a display menu generator for generating a customization menu that enables user selection of a default set of medical parameters from a plurality of available sets of default medical parameters. The customization menu further enables user modification of the default set of medical parameters. A display generator responsive to a user command operates to display the modified default set of medical parameters in a graphical or tabular format.

18 Claims, 8 Drawing Sheets

OTHER PUBLICATIONS

QS Workstation General Information.
HP M2000A Patient Documentation Center.
Metavision.
Tour Metavision.
Tour Workflow Support.
Physician Review System Functionality Comparison.
Solar Unit Manager System General Information.
HP Carevue Clinical Information System.
Tour Data Entry.
Tour Analysis.
HPM2000A Central Data Management for the Critical Care Environment.
Agilent Technologies Virdia Documentation Center.
HP Carevue Date Reporting Solution.

* cited by examiner

APPARATUS FOR PROCESSING AND DISPLAYING PATIENT MEDICAL INFORMATION

CROSS REFERENCE TO RELATED APPLICATION

This application claims the benefit of provisional U.S. application, U.S. Ser. No. 60/249,574 filed Nov. 17, 2000.

FIELD OF THE INVENTION

This invention is related to the processing and displaying of medical information, and more particularly to configuring, processing and displaying of patient medical data in a network environment.

BACKGROUND OF THE INVENTION

In hospitals and other health care environments, it is often necessary or desirable to collect and display a variety of medical data associated with a patient. Such information may include laboratory test results, care unit data, diagnosis and treatment procedures, ventilator information, attending physician or health care provider, and calendar information associated with a given patient. Presently, such information is often provided via a chart attached to a patient's bedside or at an attendant's station. However, such physical charts are cumbersome to view, and often do not include the most up-to-date medical information associated with the patient, such as laboratory test results. This problem is exacerbated due to the large amount of patient data that accumulates during a patient's stay in the hospital. Traditional paper-based charts for displaying patient medical data including chronological or timeline information are particularly cumbersome to view, difficult to organize and susceptible to page loss or misplacement. Additional problems related to the timeliness of such chart information arise from the fact that medical data often arrives from multiple sources and at various times. Furthermore, present charts are not adapted to enable a care giver to easily access, view, or determine the results of multiple medical tests or other data associated with the patient. Consequently, a need exists for a faster, more effective and user friendly means for accessing, configuring, manipulating and displaying patient medical information including physiologic parameter data and timeline information derived from a plurality of sources.

SUMMARY OF THE INVENTION

A network compatible, configurable user interface system for displaying a set of user-selectable, sequentially generated patient medical parameters, together with an associated time indication comprises a display menu generator for generating a customization menu that enables user selection of a default set of medical parameters from a plurality of available sets of default medical parameters. The customization menu further enables user modification of the default set of medical parameters. A display generator responsive to a user command operates to display a default set of medical parameters. The customization menu enables user selection of a graphical or tabular format for parameters within the default set. A display generator further operates to display a first subset of parameters within the default set in a first graphical format, and second subset of parameters within the default set in a second tabular format. The user customization menu also facilitates user definition of multiple default parameter sets for storage and later retrieval from a data base. The default sets of medical parameters include at least two associated with the following medical categories: cardiology, laboratory results, hemodynamic functions, ventilation parameters and neurology.

In another aspect, a network-compatible, configurable user interface system for displaying sequentially generated patient medical parameters together with the time indication, for use in identifying a parameter value trend comprises a display menu generator for generating a single customization menu that enables user selection of parameters for display in a first graphical format and a second tabular format. A menu containing a set of medical parameters representing a corresponding plurality of available medical parameters and first and second window areas for displaying user selected parameter labels representing parameters for display in graphical and tabular format respectively are provided within the customization menu. The menu further includes parameter selection icons enabling user selection of parameters from the available set of medical parameters for displaying graphical or tabular format. A display generator displays the parameters associated with the labels in the first window in graphical format, while displaying parameters associated with labels in the second window area in tabular format in response to a user command.

DETAILED DESCRIPTION

Figure 1:
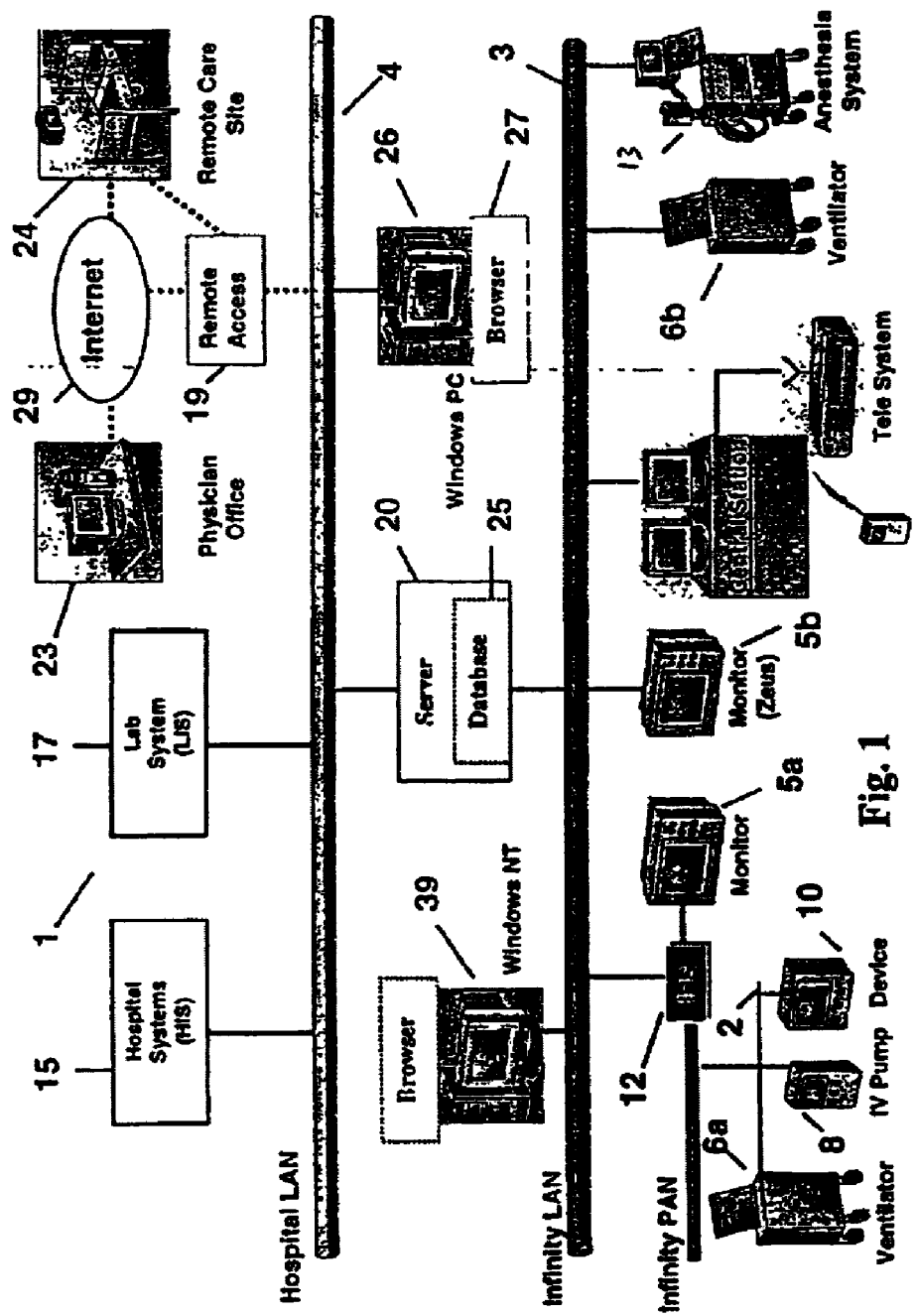
FIG. 1 is a block diagram of a communication network with various devices, according to the principles of the invention.

FIG. 1 is an exemplary block diagram of a communication network according to the principles of the present invention. Throughout the drawings, like reference numerals are used to indicate like parts. As shown in FIG. 1, communication network 1 is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown on FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a patient's room to administer care to a particular patient and to monitor the particular patient. Various medical devices may be connected via MIB 2; examples shown in FIG. 1 comprise a ventilator 6a, IV (Intravenous) Pump 8 or other medical equipment 10.

MIB 2 is typically connected to a second level LAN network 3 through an Interface Docking Station (IDS) device 12, for interfacing to Ethernet-compatible LAN network 3. The higher-level LAN 3 may be for example, an Infinity LAN, marketed by Siemens Medical System. This higher-level LAN 3 is typically, though not necessarily, used by a particular department within a hospital, such as an intensive care department or surgery department, etc., depending on the size of the organizations.

Although not shown in FIG. 1, more than one MIB may be connected to the second level LAN 3, so that more than one patient may be monitored or given care through LAN 3. In addition, medical devices may be connected directly to higher-level LAN 3. For example, as shown in FIG. 1, a ventilator 6b and an anesthesia system 13 are connected directly to LAN 3, without the need to go through a MIB.

Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 19 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 19 may also be part of server 20, to be described below, instead of standing alone, as well know in the art.

According to the principles of the present invention, a central server 20 resides on LAN 3 for gathering and processing data from the peripheral medical devices or facilities coupled to LAN 3 or hospital LAN 4, including medical parameters such as lab results supplied via lab system 17 connected through an HL7 interface, for example. Additional medical parameter data including cardiology, hemodynamic, ventilation and neurology category data may also be acquired from any number of medical devices such as those shown in FIG. 1 and may be obtained at server 20 using various interface protocols such as ASTM messaging, for example. The acquired medical parameters associated with a given patient, including cardiology, hemodynamic, ventilation and neurology category parameters and data are acquired from the medical devices on network 1 for display and control. One skilled in the art can readily recognize that server 20 may reside at any level of the hierarchy of network 1, since all the different levels of LANs (e.g., 3, or 4), as well as remote sites in FIG. 1 are interconnected together. An example of server 20, is a ChartAssist server, marketed by Siemens Medical System. The server may be hosted, for example, by a computer system that is capable of running Microsoft NT operating system.

In one aspect of the present invention, a user may use a Microsoft Windows compatible PC 26 or Windows NT compatible PC 39 as shown in FIG. 1, or any other computers capable of running a menu generating program such as a web browser program (e.g., Microsoft Internet Explorer or Netscape Navigator, etc.) to view, configure and update medical parameter data including cardiology, lab results, hemodynamic, ventilation and neurology information associated with a given patient. That is, a user may use a web browser on any computer, as long as a communication connection can be made to server 20, to make request, view and update information acquired and stored in data base 25. This is advantageous, since a doctor may for example, gain access to medical parameter data from, for example, a remote physician's office 23, without having to access a dedicated terminal. Of course, a user can simply use a keyboard and/or a mouse or any other user interface devices to enter a user selection or request on a user computer, as is known in the art.

Server 20 is capable of collating and formatting medical data to be compatible with, for example, HTML (HyperText Mark-up Language) programming language for displaying data on the web browser having a graphical user interface (GUI) component. The server is also responsive to, for example, HTTP (HyperText Transfer Protocol) commands originated from a user's web browser for making a request.

Figure 2A:
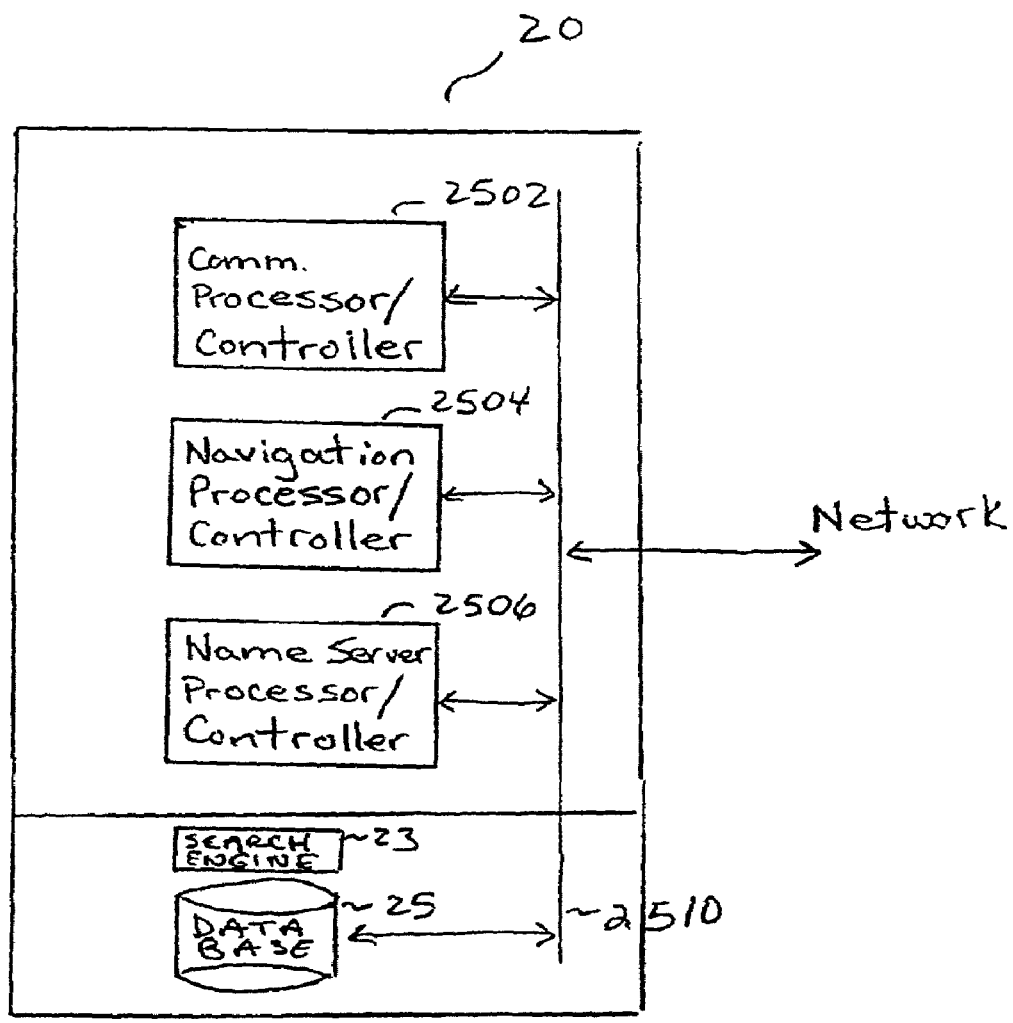
FIG. 2A is a block diagram of a server having functionality in accordance with the present invention.

FIG. 2A shows a block diagram of an exemplary embodiment of the server 20 which operates to manage, collate, search and update the data base 25 containing patient medical information. Program elements or processors operative to carry out instructions for performing the various functions described herein include communications processing module 2502 that acquires the patient data including the monitored parameters associated with a given patient from the network and collates the information for storage in data base 25. Navigation collation processor 2504 operates in conjunction with the web browser and display generator software to provide and prioritize parameters for display to the user while navigating through various applications selected by a user through the user interface.

Figure 2B:
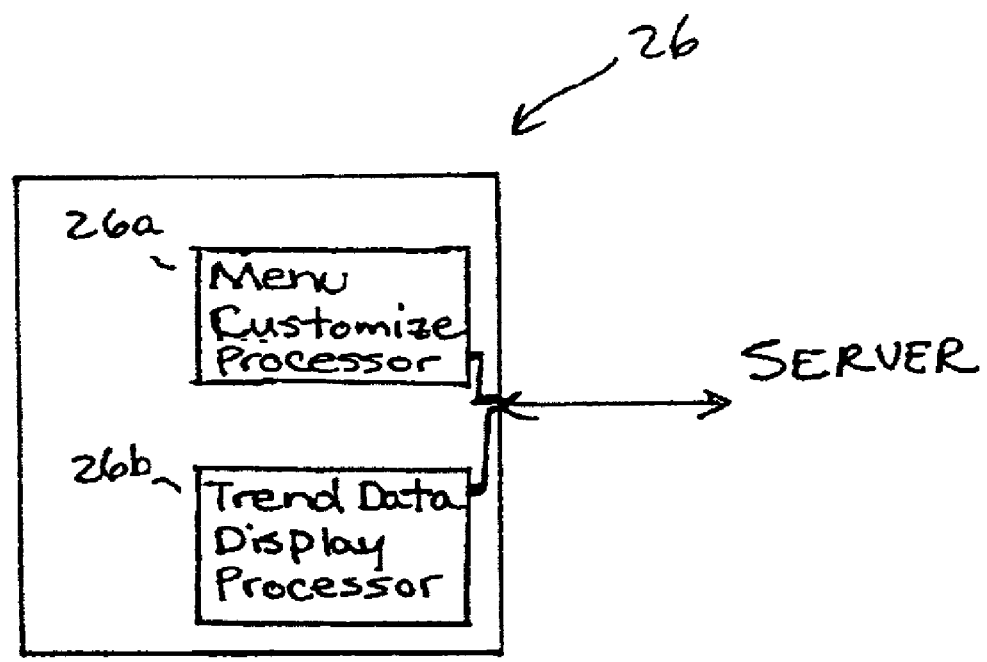
FIG. 2B is a block diagram of program elements associated with the user interface computer and web browser in accordance with the present invention.
Figure 2G:
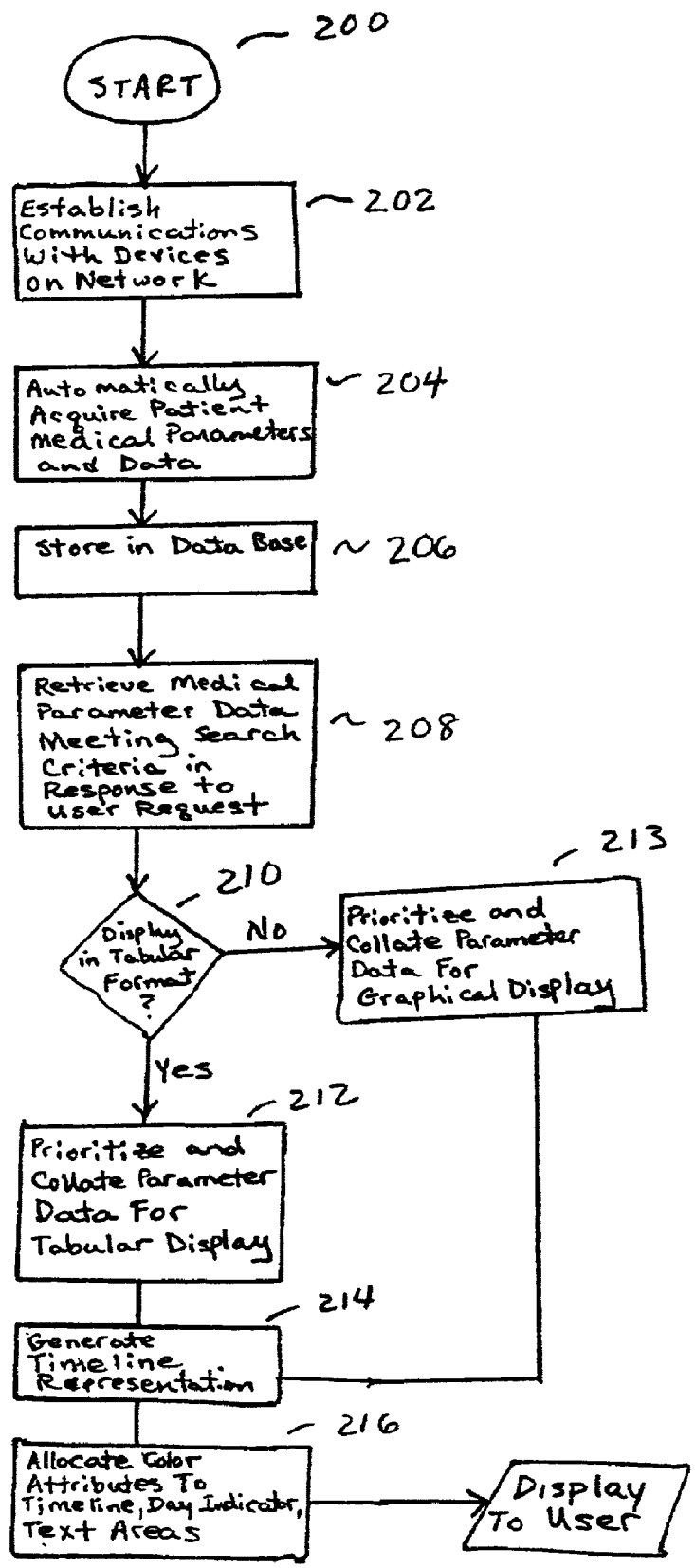
FIG. 2C is a flow diagram of system processing functions in accordance with the present invention.

The user interface contains functionality for displaying medical data along a timeline in response to user selection and for pre-configuring and formatting the medical data parameters to be displayed. Program elements or processors operative to carry out instructions for performing the various functions associated with the user interface computer processor 26 and web browser in conjunction with server software are shown in FIG. 2B and include menu generator processor module 26a for generating a customization menu that enables a user to preconfigure multiple categories of physiologic trend data for display, and a display generator module 26b for displaying selected physiologic trend data according to the preconfigured selections in response to a user command.

Name server processor 2506 (FIG. 2A) associates unique identifiers (Ids) with each node connected to the system network and with each patient in the system in order to track and update patient information throughout the system. Input/output data and control signals are used to communicate between the various processors as well as to interface with the data base 25 and search engine 23 and with the network via communication line 2510.

FIG. 2C illustrates an exemplary flow diagram wherein medical parameter data including cardiology, lab results, hemodynamic, ventilation and neurology category data may be continuously or periodically acquired and correlated with a given patient for storage in relational data base 25 within server 20. Data base 25 may be of the type used for storing relational data such as the Microsoft SQL server. Upon establishing communication with the devices on the network (step 202), data may be automatically or periodically acquired and stored in data base 25 (steps 204, 206). The acquired data may include time stamp information or other information indicative of the date and time associated with the acquired data. A user request for medical parameter data associated with a given patient (step 208) causes the search engine on server 20 to search and retrieve all data parameters meeting the predetermined search criteria. The user request includes parameters related to the collation and display of the data in a predetermined format and in a selected day range. If a tabular format is requested (step 210) user interface software logic operates to collate and prioritize the retrieved data for display in column fashion (step 212). Otherwise, the user interface software collates and prioritizes the retrieved data for display in graphical fashion (step 213). In addition, a timeline representation associated with the data parameters to be displayed is generated and formatted (step 214) for display with the data. Software logic within the user interface allocates color attributes to the timeline, display text areas, and user selection indicator panel for differentiating parameter data over day boundaries (step 216). A display generator then operates to display a composite window containing patient medical data and parameters together with timeline information and color attributes connecting the data with the selected day.

Figure 3A:
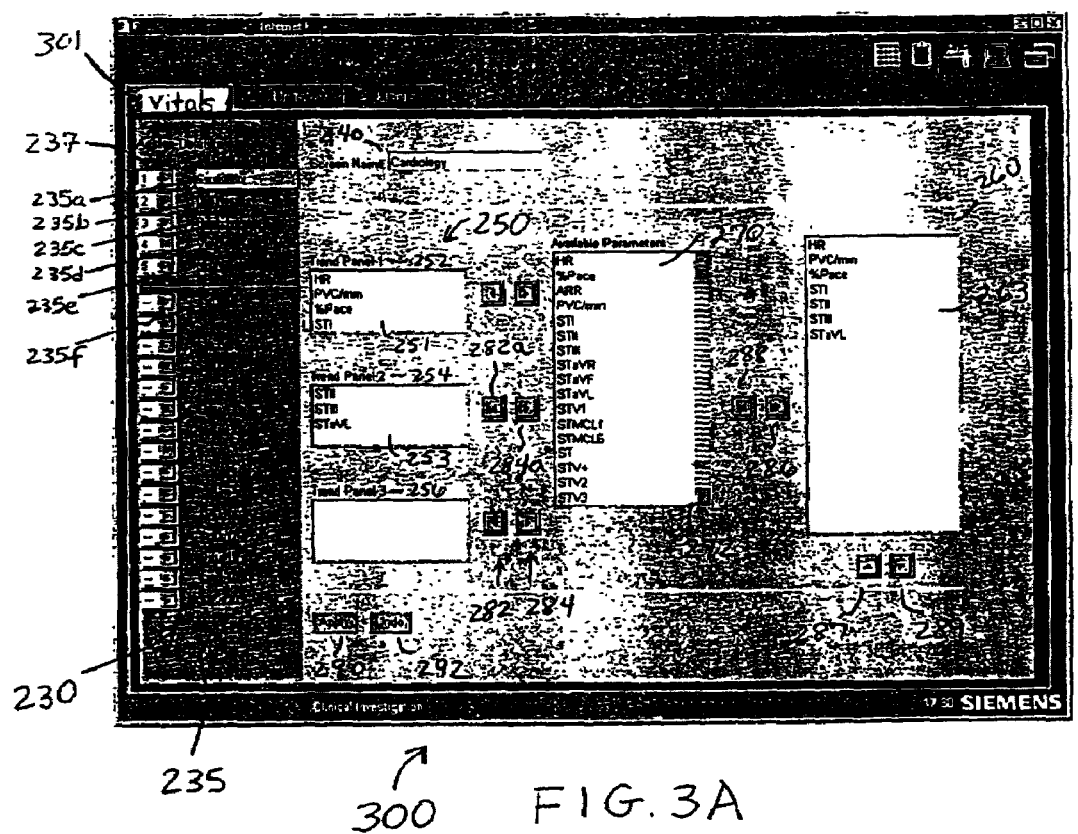
FIG. 3A shows an exemplary way of how default system medical parameters are configured according to an aspect of the present invention.

FIG. 3A is an exemplary illustration of a user interface system embodied in an aspect of the present invention for configuring trend display information at a system level. As shown in FIG. 3A, a customization menu 300 is displayed in response to execution of the menu generator process by a system user having appropriate network authority and logon privileges such as a system administrator. Single customization menu 300 permits a user to define default trend configurations for the system by editing trend display configurations for any or all of the system trend pages. According to an aspect of the invention, customization menu 300 includes a selectable menu 230 of display parameter categories 235 including for example, cardiology 235a, lab results 235b, hemodynamic 235c, ventilation 235d and neurology 235e parameter data categories, as well as additional user-definable categories 235f. Each of the categories 235 may have associated therewith a predetermined list of selected medical parameters stored in data base 25 that operate as default parameter sets.

For example, user selection of the cardiology category 235a from the list of available categories causes the system to retrieve from data base 25 the entire list of available parameters 270 associated with this category for display in scrollable menu window 272. Category label field 240 associates a name for the selected category to be edited/defined. As shown, user selection of category label 235a causes the category label "cardiology" to appear in field 240. The order in which the categories are to be displayed in the graphical and tabular trends pages is indicated by user-selectable field 237 which shows-each of the system-defined categories labeled as 1–5. User selection of a given category and editing of this field value causes the categories to be reordered according to the user-entered value.

Graphical window area 250 contains selected sets of parameters 251, 253 for graphical display and comprises first window 252 (Trend Panel 1), second window 254 (Trend Panel 2) and third window 256 (Trend Panel 3). Each window can accommodate up to four parameters. Parameter selection icons or controls comprising left and right arrow keys 282, 284 enable user selection of the parameters to be displayed from the super-set of possible parameters 270. For example, adding a parameter to Trend Panel 2 is accomplished by highlighting any one of the parameter names in menu list 272 and then clicking on the left arrow selection key 282a. In similar fashion, removing a parameter from Trend Panel 2 is accomplished by highlighting one of the parameter names from the list window 254 and then clicking on the right arrow selection key 284a. Left and right arrow keys having identical functionality are provided for each corresponding trend panel as shown.

Tabular window 260 identifies parameters 263 selected from the list of available medical parameters 270 for display in a tabular format. Right arrow key selection icon 286 operates to add a selected parameter from menu 272 to tabular window 260 while left arrow key 288 operates to remove a selected parameter from tabular window 260. Variation and determination of the display order of the parameters is accomplished by up and down arrow keys 287, 289 which operate to move a highlighted parameter in list 260 up or down the list of parameters according to the user. Note that the customization screen functions to enable a user to configure tabular trend displays and graphical trend displays independently. That is, different sets of selected parameters 251, 253 can be selected and configured for graphical display while other sets of parameters 263 can be selected and configured for tabular display. This advantageously permits a user to view different parameters using different display sets, thereby enabling a more robust, customized display of trend data.

Selection of "apply" control function 290 causes the system to store the user selected parameters for the named category as default system parameters for that category. The system also operates to store the edited or determined parameter display order, the assignment of each category name to a given page, and the order of display of the category names. Selection of control function 292 cancels the user selection and exits the screen without saving the edited data.

Figure 3B:
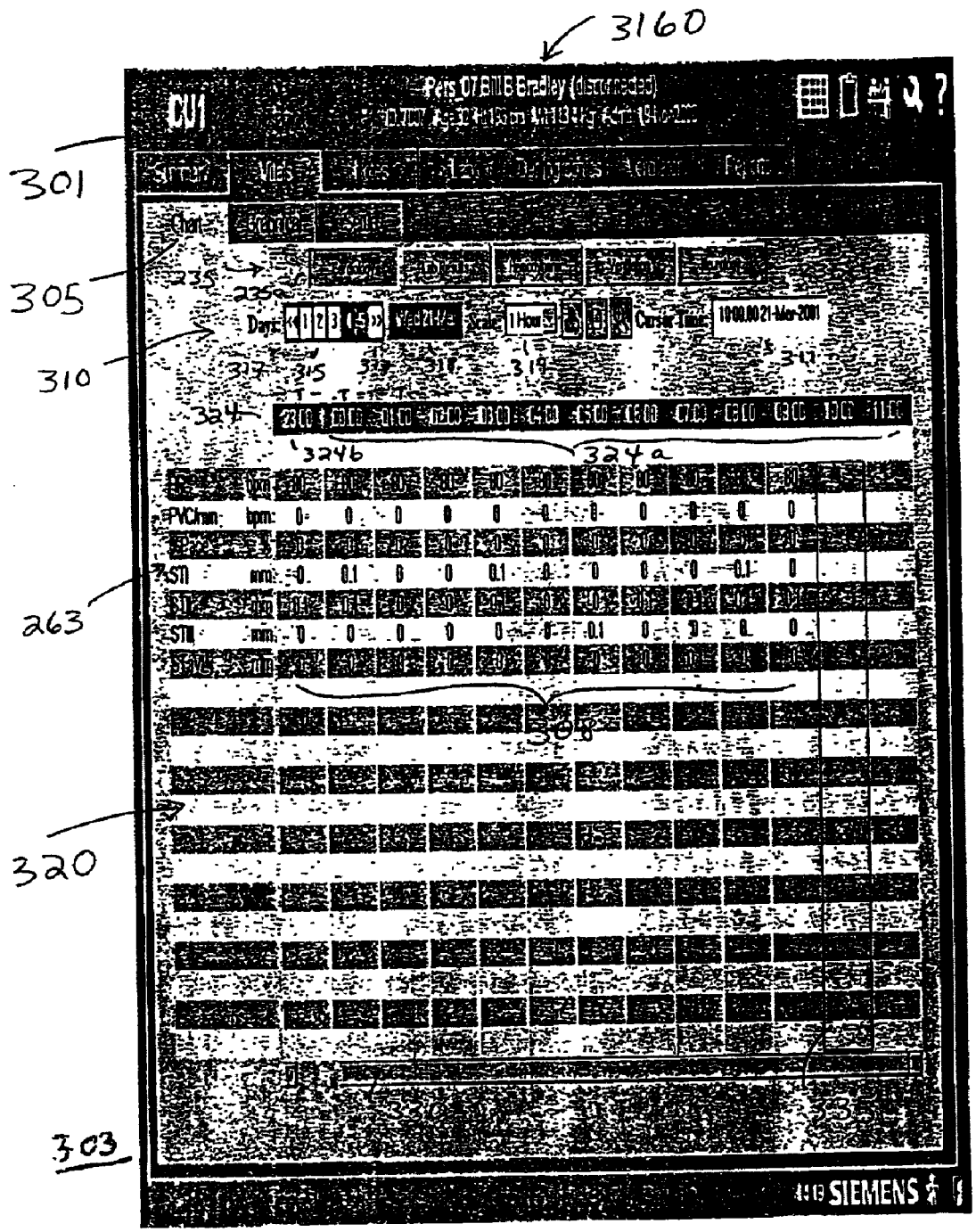
FIGS. 3B and 3C are exemplary illustrations of medical parameters displayed in tabular and graphical formats, according to the configured system parameters selected and applied in FIG. 3A
Figure 3C:
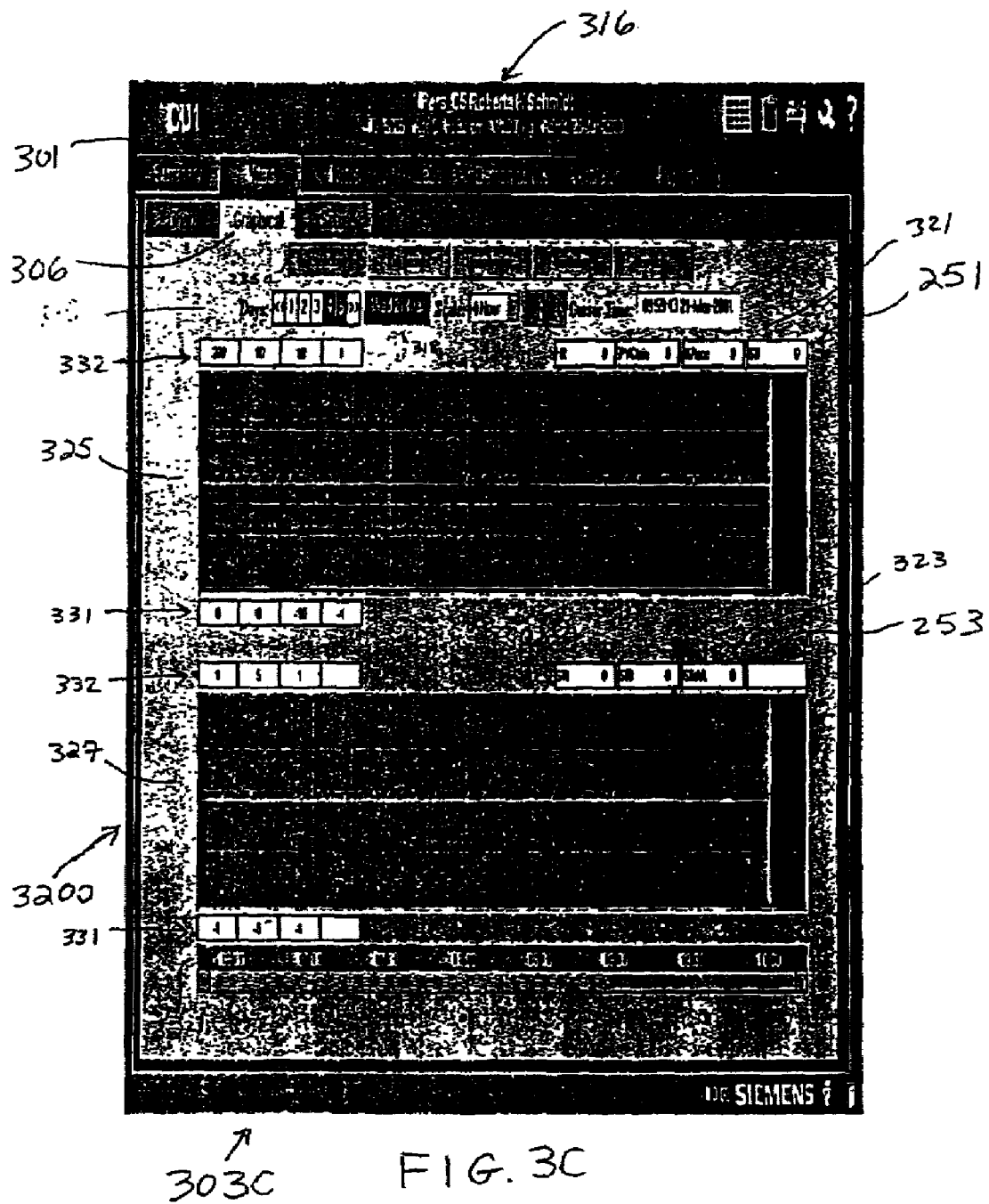

FIGS. 3B and 3C are exemplary illustrations of web browser screens displaying in tabular and graphical formats, respectively, the configured parameters selected and applied to the system by the method of FIG. 3A.

Referring now to FIG. 3B, there is shown a display window 303 containing medical parameter data associated with particular monitored parameters 263 retrieved and displayed on a web browser of a user computer 26 (FIG. 1) along a timeline spanning multiple days to enable a user of the system to view trend information, according to the present invention. As shown, display window 303 (FIG. 3B) comprises navigator panel portion 310 and a results display window portion 320. Display window 320 contains the particular medical parameters 263, units of measure, and data 308 displayed in accordance with the configured format (FIG. 3A) along timeline 324 (FIG. 3B) in response to a user request for access to particular medical parameter data associated with a given patient. The medical parameter data shown in FIG. 3B is displayed in display window 320 in tabular (i.e. chart) format when the user selects chart icon 305 from the vitals panel 301. Selection of one of the icons labeled generally as 235 and corresponding to particular medical parameters associated with a corresponding one of cardiology, lab results, hemodynamic, ventilation and neurology categories causes the user interface to request a search of the data base to obtain those particular medical parameters within the category selected. When the cardiology category 235a is selected, the display generator then displays the results as shown in accordance with the configured default settings for cardiology parameters and data in tabular format.

Display navigator panel 310 comprises a scrollable, user selectable day indicator panel 315 containing the entire number of days (i.e. calendar days) that a patient has been admitted according to the data base information associated with that given patient. In an exemplary embodiment, five days (1, 2, 3, 4, 5) are displayed via day indicator panel 315 with directional control selectors 317 embodied in the form of left and right arrow buttons on either side of the display indicator panel to enable a user to scroll through the entire range of days. User selection of a particular day within the day indicator panel day range causes the search engine to retrieve from data base 25 (FIG. 1) all medical parameter data for a given patient associated with the selected day, the immediately preceding day, and immediately succeeding day, that also meet all other search criteria (e.g. category of medical parameter data).

As shown in FIG. 3B, medical parameters 263 and accompanying data 308 are displayed to the user in tabular form across day boundaries in response to user selection of a particular day (e.g. Day 5) within day indicator panel 315. The user interface operates to generate timeline display 324 having a first portion 324a associated with the current or selected day and a second portion 324b associated with the previous or next day. In a particular embodiment, the timeline 324 is segmented into predetermined intervals T of equal duration. These intervals are scalable in user selectable increments of 15 minutes, 1 hour, 2 hours, 4 hours or 8 hours based on user selection of scale panel 319 and formatted for display in window 320. The timeline display includes indicia in hour/minute (hh:mm) format enabling a user to identify the particular time associated with particular corresponding displayed parameter data, as well as enabling a user to view or determine trends associated with the patient medical data. The retrieved medical data is prioritized, collated and displayed in a desired order in accordance with the search criteria.

In the embodiment shown in FIG. 3B, medical parameters 263 comprising Heart Rate (HR) PVC/min, %Pace, STI, STII, STIII and STaVL are displayed in descending order along a first column according to the configured cardiology tabular default system trend setup while the corresponding data associated with each of the parameters are displayed in time sequence fashion along the horizontal or row. The data is aligned with the timeline display to associate a temporal period with a given column's parameter data. The right most data displayed via the web browser represents the most recent medical parameter data. The system is also operative to provide a separate cursor time display window 311 responsive to user selection of a given column 335 for displaying the date and time associated with the position of the cursor. Horizontal scrollbar 330 positioned at the bottom of the display enables a user to view additional timeline data that cannot fit within the viewable display, due for example to the interval scaling.

As part of the user interface apparatus of the present invention, a software module or wizard operative for displaying window 303 to the user includes logic for allocating a display attribute to the current or selected day within the day indicator panel 315. In an exemplary embodiment of the invention, the display attribute comprises a color, but may also be a text or symbol, a geometric shape or style, or a font type, for example. As shown in the exemplary embodiment of FIG. 3, the selected day (i.e. Day 5) has a blue background, while the immediately adjacent day (e.g. Day 4) for which medical parameter data exists is displayed having a black background. Days for which no data is displayed (e.g. Days 1,2,3) are displayed having a white background. A text area 318 adjacent the day indicator panel 315 displays calendar date information associated with the currently selected day. In an exemplary embodiment, the calendar date information includes the particular day of the week (e.g. Sun.–Sat.), month, and date. Advantageously, the background associated with text area 318 has the same display attribute (e.g. the same blue color) as the currently selected day.

The timeline display portion 324a associated with the currently selected day is distinguishable from portion 324b associated with the previous and/or subsequent day due to its use of the display attribute. In an exemplary embodiment, the background of the timeline display matches with the background of the day indicator panel for the corresponding day. For example, as shown in FIG. 3B, display portion 324a includes a blue background attribute corresponding to the blue background attribute of the currently selected day, while display portion 324b includes a black background corresponding to the black background attribute of the succeeding day (i.e. Day 5). Given the large amount of patient data that can exist for the patient's length of stay, it is not feasible to download the entire data set to the browser. Similarly, due to the continuous nature of the data being viewed, allowing the user to view data one day at a time is inefficient. The user interface apparatus of the present invention overcomes these difficulties by providing a scrollable window display extending beyond a single day (i.e. 24 hour period) while allowing a user to select a desired day and enabling the user to differentiate the days that are represented on the timeline.

FIG. 3C illustrates an alternative component display within the web enabled GUI system of the present invention for displaying in graphical format medical data associated with particular parameters as defined by the graphical default system configuration shown in FIG. 3A. As previously discussed, the medical parameters and data are retrieved and displayed on a web browser of a user computer 26 along a timeline spanning multiple days. For brevity, a discussion of the same functionality associated with the same components shown and discussed with respect to FIG. 3B has been omitted.

FIG. 3C shows graphical trend display window 3030 comprising navigator panel portion 310 and results display window portion 3200 containing corresponding parameters 251, 253, units of measure and medical parameter data 3080 displayed in graphical format along timeline 324 in response to a user request for access to particular medical parameter data associated with a given patient. In the exemplary embodiment shown in FIG. 3C, the medical parameter data is displayed in graphical format when the user selects Graphical icon 306 from the vitals panel 301 for displaying the medical data associated with the cardiology category. User selection of the day indicator panel 315 operates as described above with respect to FIG. 3B to enable retrieval and display of all medical parameter data for a given patient associated with the selected day, the immediately preceding day, and immediately succeeding day, that also meet all other search criteria (e.g. category of medical parameter data).

As shown in FIG. 3C, the user interface display for displaying the particular medical parameters and data operates to collate certain parameters and data for grouping together for display in a desired order according to the pre-configured graphical default criteria. For example, the embodiment shown in FIG. 3C provides for two displays or trend panels 325, 327 (FIG. 3C) each including a graphical representation of particular patient medical data corresponding to the parameters selected in windows 252, 254 (FIG. 3A) along horizontal timeline 324. As shown, each trend panel 325, 327 comprises a maximum of 4 trends or sets of medical parameters for display along the graph. Display windows 321, 323 positioned above each of the trend panels identify the corresponding medical parameters whose data are graphically displayed along the timeline. Each display window has a particular attribute (such as a color attribute) that corresponds to a same attribute associated with the corresponding graphical data. For example, the display window which represents monitored the Heart Rate (HR) parameter, has a red background so as to correspond in one-to-one fashion with the red colored graphical representation of the HR parameter data. The other display windows have a correspondingly distinct color attribute associated with the same color attribute of their particular graphical data to enable a user to distinguish parameter trends. Other attributes are also contemplated, including font, style, geometry and the like.

Parameter range display sets 331, 332 provide minimum and maximum ranges respectively associated with each of the corresponding medical display parameters. In a particular embodiment, the range display set is provided with the maximum and minimum range limits 332, 331 located on the left hand side above and below, respectively the graphical parameter data window. As shown in FIG. 3C, the maximum and minimum range scale limits for each parameter appear in a differentiated color and in the specific order in which the parameter labels are presented.

Figure 3D:
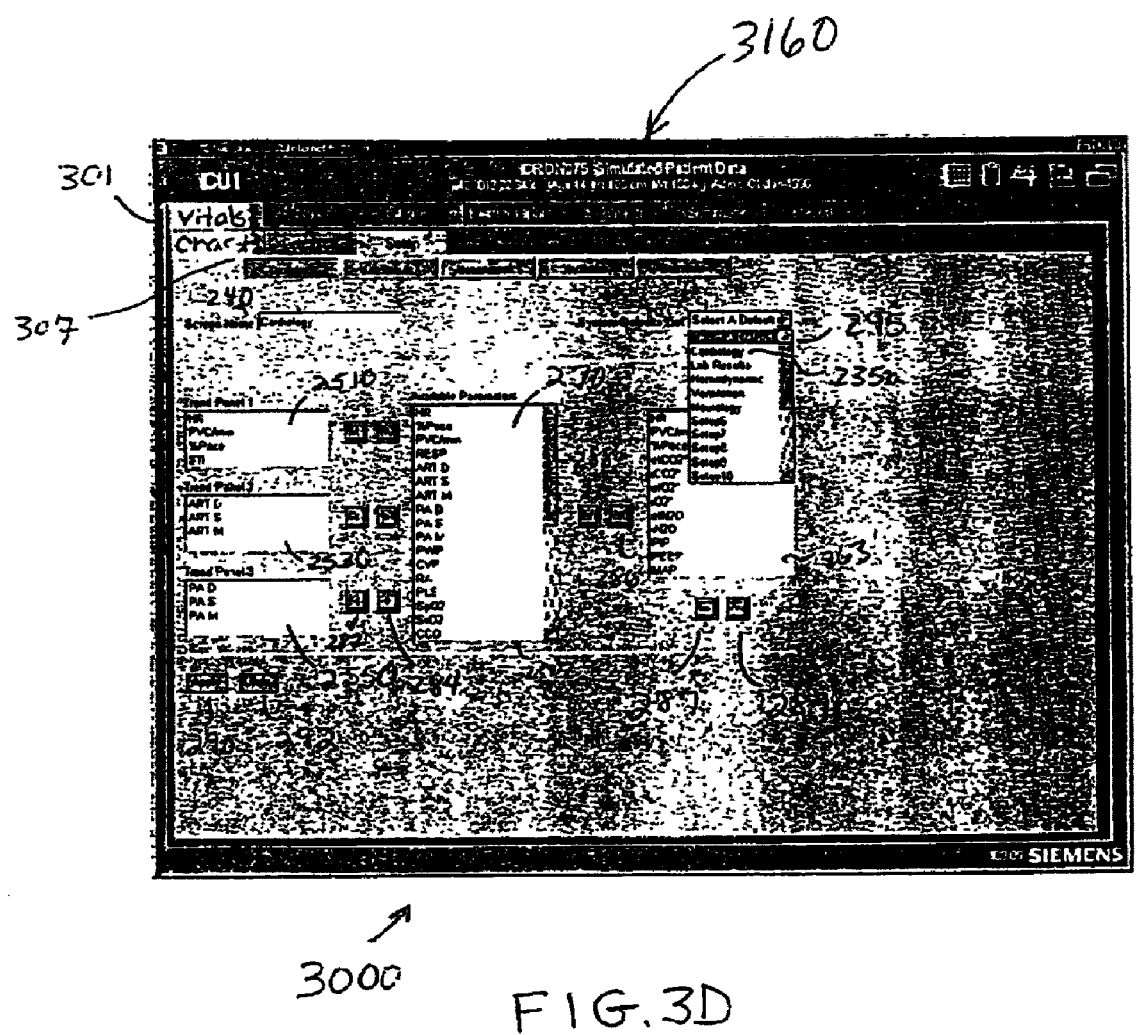
FIG. 3D shows an exemplary way of how medical parameters are configured for a given user according to an aspect of the present invention.

FIG. 3D illustrates an alternate aspect of the present invention for customizing trend information at a patient level. This is accomplished by selecting, for a given patient 3160, setup tab 307 for displaying customization menu 3000. For brevity, a detailed discussion of the same functionality associated with the same components shown and discussed with respect to FIG. 3A has been omitted. As shown, a user, other than a system administrator, may customize the trend configurations for a given patient to display a list of currently active parameters by selecting a preconfigured trend page (e.g. cardiology) via system default menu 295, selecting particular parameters 2510, 2530, 2550 for display from a list 270 of parameters that are currently active for that patient, determining the order in which such active parameters are to appear, or editing the name of the selected trend page in field 240. Selection of the "apply" control function 290 causes the system to store this preconfigured file associated with this patient such that subsequent selection of the particular trends application for this patient (e.g. Vitals-Chart for patient 3160) causes the display generator to display selected parameters or subsets of the default set associated with the customized preconfigured file for that user rather than the system default configuration.

It is to be understood that the embodiments and variations shown and described herein are for illustrations only and that various modifications may be implemented by those skilled in the art without departing from the scope of the invention.

What is claimed is:

1. A network compatible configurable user interface system for displaying sequentially generated patient medical parameters and data together with a time indication, for use in identifying a parameter value trend, comprising:
a display menu generator for generating,
a single customization menu enabling user selection of parameters for display in a first graphical format and in a second tabular format comprising,
a menu containing a set of medical parameter labels representing a corresponding plurality of available medical parameters,
a first window for displaying a list of user selected ones of said plurality of available medical parameter labels to be displayed in a graphical format,
a second window for displaying a list of user selected ones of said plurality of available medical parameter labels to be displayed in a tabular format, and
parameter selection icons enabling user selection of medical parameter labels from said menu and display of said selected medical parameter labels in a selected one of said first and second windows, wherein a user is able to configure a user interface image display by selecting a first of said medical parameter labels from said menu for display in said first window and display of a medical parameter associated with said first of said medical parameter labels exclusively in graphical format and a second of said medical parameter labels from said menu for display in said second window and display of a medical parameter associated with said second of said medical parameter labels exclusively in tabular format; and
a display generator for displaying said user selected parameters in graphical and tabular format in response to a user command.

2. The system of claim 1, wherein said parameter icons are used to select parameters from said available medical parameters for display in graphical and tabular format by incorporating selected parameters in said first and second windows of said customization menu, and
said display generator displays parameter data associated with parameters in said first window in graphical format and displays parameter data associated with parameters in said second window in tabular format, in response to said user command.

3. The system of claim 1, wherein said customization menu enables allocation of a plurality of different sets of selected parameters to a corresponding plurality of display categories.

4. The system of claim 3, wherein said categories include at least two associated with medical categories including cardiology, laboratory results, hemodynamic function, ventilation function and neurology.

5. The system of claim 3, wherein said customization menu enables display of at least one predetermined list of selected parameters associated with a particular display category.

6. The system of claim 1, wherein said single customization menu further comprises placement selection icons for re-ordering display of selected parameters.

7. The system of claim 1, wherein said single customization menu further comprising category selection icons for re-ordering display of the available categories of medical parameters for user selection.

8. The system of claim 1, wherein a user is able to select a third of said medical parameter labels from said menu for display in said first window for display in graphical format and said second window for display in tabular format.

9. A network compatible configurable user interface system for displaying a set of user selectable sequentially generated patient medical parameters and data together with an associated time indication, comprising:

a display menu generator for generating,
    a customization menu enabling user selection of a default set of medical parameters from a plurality of available sets of default medical parameters and user modification of said default set of medical parameters, said customization menu including:
        a menu containing a set of medical parameter labels representing a corresponding plurality of available medical parameters,
        a first window for displaying user selected ones of said plurality of available medical parameter labels to be displayed in a graphical format,
        a second window for displaying user selected ones of said plurality of available medical parameter labels to be displayed in a tabular format, and
        parameter selection icons enabling user selection of medical parameter labels from said menu and display of said selected medical parameter labels in a selected one of said first and second windows, wherein a user is able to configure a user interface image display by selecting a first of said medical parameter labels from said menu for display in said first window and display of a medical parameter associated with said first of said medical parameter labels exclusively in graphical format and a second of said medical parameter labels from said menu for display in said second window and display of a medical parameter associated with said second of said medical parameter labels exclusively in tabular format; and
    a display generator for displaying said user-modified default set of medical parameters in response to user command.

10. The system of claim 9, wherein said customization menu enables user definition of a plurality of default parameter sets.

11. The system of claim 9, wherein said plurality of available sets of default medical parameters include at least two associated with medical categories including cardiology, laboratory results, hemodynamic function, ventilation function and neurology.

12. The system of claim 9, wherein said single customization menu further comprises placement selection icons for re-ordering display of selected parameters.

13. The system of claim 9, wherein said single customization menu further comprises category selection icons for re-ordering display of available categories of medical parameters for user selection.

14. The system of claim 9, wherein a user is able to select a third of said medical parameter labels from said menu for display in said first window for display in graphical format and said second window for display in tabular format.

15. A network compatible configurable user interface system for displaying sequentially generated patient medical parameters and data together with a time indication, for use in identifying a parameter value trend, comprising:

a display menu generator for generating,
    a single customization menu enabling user selection of parameters for display in a first graphical format and a second tabular format comprising,
        a menu containing a set of medical parameter labels representing a corresponding plurality of available medical parameters,
        first and second window areas for displaying user selected parameter labels to be displayed with associated parameter data in graphical and tabular format respectively, and
        parameter selection icons enabling independent user selection of parameters from said available medical parameters for display in graphical format and independent user selection of parameters from said available medical parameters for display in tabular format, wherein a user is able to configure a user interface image display by selecting a first of said medical parameter labels from said menu for display in said first window area and display of a medical parameter associated with said first of said medical parameter labels exclusively in graphical format and a second of said medical parameter labels from said menu for display in said second window area and display of a medical parameter associated with said second of said medical parameter labels exclusively in tabular format; and
    a display generator for displaying parameter data associated with parameters in said first window area in graphical format and for displaying parameter data associated with parameters in said second window area in tabular format in response to a user command.

16. The system of claim 15, wherein said single customization menu further comprises placement selection icons for re-ordering display of selected parameters.

17. The system of claim 16, wherein said single customization menu further comprises category selection icons for re-ordering display of available categories of medical parameters for user selection.

18. The system of claim 15, wherein a user is able to select a third of
    said medical parameter labels from said menu for display in said first window for display in graphical format and said second window for display in tabular format.

* * * * *